(12) United States Patent
Heitmann

(10) Patent No.: US 7,880,482 B2
(45) Date of Patent: Feb. 1, 2011

(54) SENSOR MECHANISM AND METHOD FOR THE PRODUCTION THEREOF

(75) Inventor: Michael Heitmann, Bielefeld (DE)

(73) Assignee: Miele & Cie. KG, Guetersloh (DE)

( * ) Notice: Subject to any disclaimer, the term of this patent is extended or adjusted under 35 U.S.C. 154(b) by 649 days.

(21) Appl. No.: 11/993,382

(22) PCT Filed: Jun. 8, 2006

(86) PCT No.: PCT/EP2006/005466

§ 371 (c)(1),
(2), (4) Date: Dec. 20, 2007

(87) PCT Pub. No.: WO2006/136293

PCT Pub. Date: Dec. 28, 2006

(65) Prior Publication Data

US 2010/0277187 A1    Nov. 4, 2010

(30) Foreign Application Priority Data

Jun. 21, 2005   (DE) .................. 10 2005 029 047

(51) Int. Cl.
   *G01R 27/08*   (2006.01)
   *G01N 27/02*   (2006.01)

(52) U.S. Cl. .................. 324/693; 324/445; 324/722

(58) Field of Classification Search .................. 324/693, 324/445, 722

See application file for complete search history.

(56) References Cited

U.S. PATENT DOCUMENTS

| 3,396,331 | A | | 8/1968 | Sperry, III |
| 4,138,639 | A | * | 2/1979 | Hutchins ................. 324/442 |
| 4,740,755 | A | * | 4/1988 | Ogawa .................... 324/445 |
| 5,959,455 | A | | 9/1999 | Brown |
| 7,405,572 | B2 | * | 7/2008 | Quackenbush et al. ...... 324/445 |

FOREIGN PATENT DOCUMENTS

| DE | 371811 | 3/1923 |
| DE | 10005491 | 3/2005 |
| GB | 2191293 | 12/1987 |
| GB | 2226141 | 6/1990 |
| SU | 418782 | 3/1974 |

* cited by examiner

*Primary Examiner*—Amy He
(74) *Attorney, Agent, or Firm*—Leydig, Voit & Mayer, Ltd.

(57) ABSTRACT

A sensor device and a method of making a sensor device. The sensor device includes a coil arrangement including a primary coil and a secondary coil. A conduit that is traversable by a flow in a figure-8 pattern is disposed as a yoke about the coil arrangement such that the coil arrangement is disposed in a vicinity of an intersection of the figure-8 pattern. The conduit includes at least two parts. A parting plane of the two parts is configured so as to enable the coil arrangement to be slip-fit mounted on the conduit before the two parts are joined together.

20 Claims, 4 Drawing Sheets

SENSOR MECHANISM AND METHOD FOR THE PRODUCTION THEREOF

CROSS REFERENCE TO RELATED APPLICATIONS

This is a U.S. National Phase application under 35 U.S.C. §371 of International Application No. PCT/EP2006/005466, filed on Jun. 8, 2006, and claims the benefit of German Patent Application No. 10 2005 029 047.7, filed on Jun. 21, 2005. The International Application was published in German on Dec. 28, 2006 as WO 2006/136293 A1 under PCT Article 221(2).

FIELD OF THE INVENTION

The present invention relates to a sensor device, in particular a conductivity sensor for a dishwasher, including a conduit which can be traversed by a flow in a figure 8 pattern and which, as a yoke, surrounds a coil arrangement including a primary coil and a secondary coil and being located in the region of the intersection of the "8". The present invention further relates to a method for producing a sensor device.

BACKGROUND

German Patent Publication DE 100 05 491 A1 describes a device for measuring the electrical conductivity of liquids using an inductive method in which a closed conduit made of non-conductive material is provided which can be traversed by fluid flow. This conduit is in the shape of an "8", and the loop is routed twice through ring cores. The conduit is traversed by a liquid to be measured, and an AC voltage is applied to a first coil, thereby inducing a voltage in a second coil, the induced voltage being usable to determine the conductivity of the fluid. Such devices are usually manufactured using chip-cutting methods, which involves a high level of manufacturing complexity and, in addition, results in high flow losses, which have to be compensated by a higher pumping capacity.

Sensor devices in which immersion sensors are provided which are integrated into an existing piping system can also be used to measure the conductivity of liquids. However, such sensor devices measure not only changes in conductivity in the fluid, but rather in the entire circulation system. When used in dishwashers, such sensor devices produce different measurement values due to the fact that dishwashers are loaded with conductive utensils made of metal and with non-conductive items.

SUMMARY

In view of the above, an aspect of the present invention is to provide a sensor device which is relatively easy to manufacture and offers relatively little resistance to flow.

In an embodiment, the present invention provides a sensor device and a method of making a sensor device. The sensor device includes a coil arrangement including a primary coil and a secondary coil. A conduit that is traversable by a flow in a figure-8 pattern is disposed as a yoke about the coil arrangement such that the coil arrangement is disposed in a vicinity of an intersection of the figure-8 pattern. The conduit includes at least two parts. A parting plane of the two parts is configured so as to enable the coil arrangement to be slip-fit mounted on the conduit before the two parts are joined together.

BRIEF DESCRIPTION OF THE DRAWINGS

The present invention will be explained in more detail below with reference to an exemplary embodiment and the accompanying drawings, in which.

DETAILED DESCRIPTION

Figure 1:
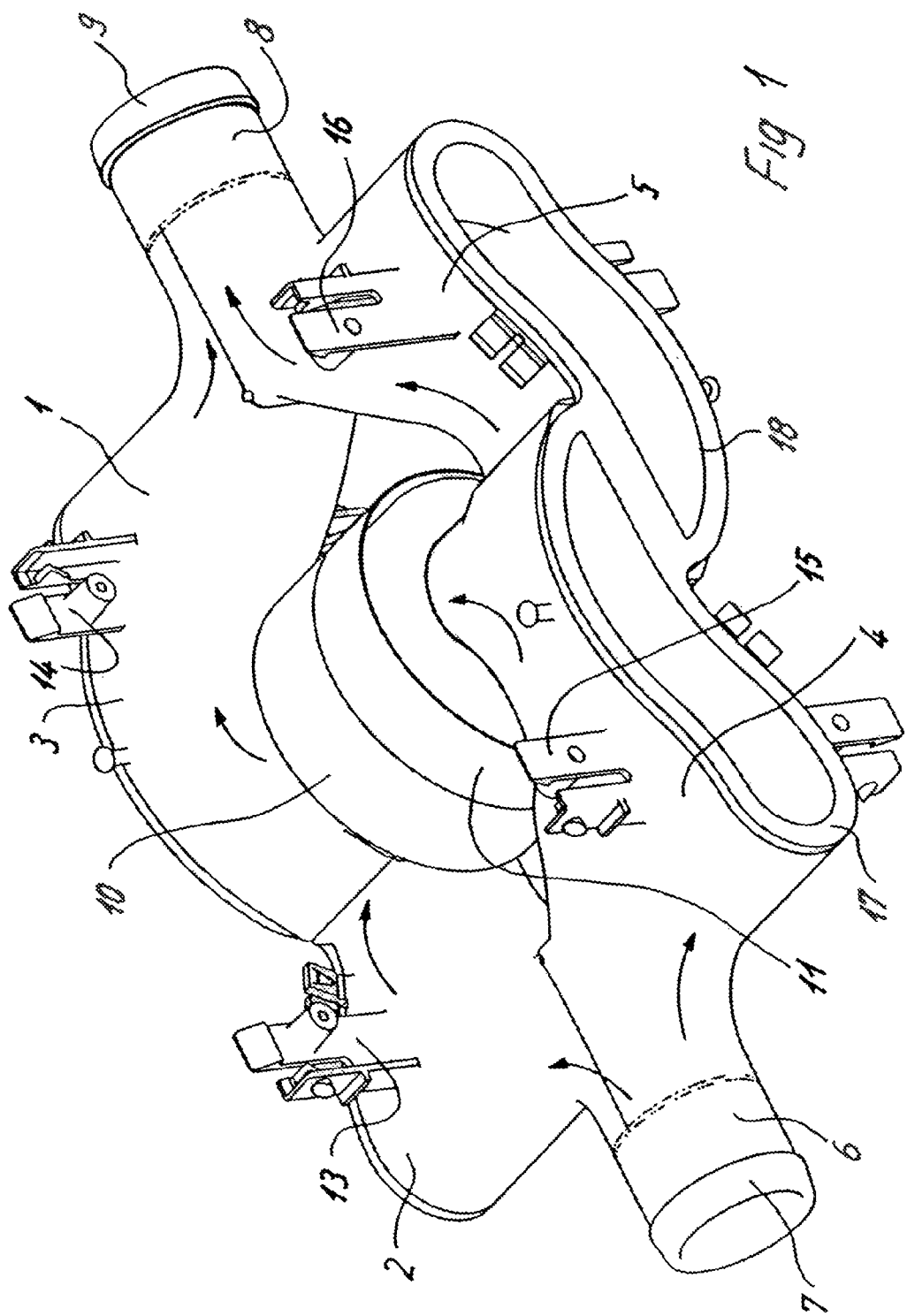
FIG. 1 is a perspective view showing a sensor device according to the present invention in the assembled condition.

In accordance with an embodiment of the present invention, the conduit is formed by at least two parts, and a parting plane of the two parts is disposed such that it allows the coil arrangement to be slip-fit mounted before the two parts are joined together, so that the sensor device is easy to manufacture, and the individual parts can be assembled in a cost-optimized manner in an industrial mass production process. In addition, the welded-together housing parts keep frictional losses low and can provide an optimized flow path. The use of plastic materials also has the advantage that even aggressive media can be traversed by the sensor device, and that the conductivity of the traversing fluid can be measured in a virtually wear-free manner.

In accordance with an embodiment of the present invention, the parting plane of the housing parts is perpendicular to the plane defined by the "8". Thus, two or four identically constructed housing parts can be joined together in the region of the parting plane in order to provide the housing with a closed flow section. In the region of the intersection of the "8", the conduits traversed by fluid may be separated from each other, because in this way, it is possible to optimize the flow characteristics of the housing, and the fluid flow from an inlet to an outlet is divided into two parts which pass through the housing in a wavy pattern. In this manner, flow losses caused by vortices are largely prevented.

In another embodiment of the present invention, an inlet is formed on a first loop and an outlet is formed on a second loop, the inlet and outlet preferably being disposed on opposite sides. The inlet and outlet may have welded thereto a tubular port for connection of a supply line or discharge line, respectively. This allows a sealing connection to be obtained between the supply line and the tubular inlet port and between the discharge line and the tubular outlet port. Otherwise, surface irregularities of the material in the region of the parting plane could cause tightness problems.

In order to optimize the production in terms of cost-effectiveness, four identical housing parts may be provided which are each joined together with a cover to form a closed conduit. These covers can engage with the housing parts to form curved flow paths, so that the flow path passes through the housing in a wavy pattern.

In addition, in order to achieve a compact design, the housing parts may be formed with holding arms for attachment of a printed circuit board.

In accordance with a method of the present invention for producing a sensor device, first, at least one coil is slipped onto a central conduit portion of a first housing part, after which the first housing part is welded to a second housing part, so that the housing parts that have been welded together form a section of a branched conduit which can be traversed by a flow in a figure 8 pattern. The first and second housing parts may also have a multi-piece design, so that, for example, four housing parts are welded together; it also being possible to mechanically join two each of the housing parts together, for example, by a clamped connection or a snap-fit connection. The method of the present invention is particularly well suited for industrial mass production, allowing a sensor device to be produced at low cost and such that the frictional losses in the flow channel are kept low.

To allow for secure attachment of a supply line and a discharge line, an inlet and an outlet of the housing parts each may have a tubular port welded thereon to which the supply and discharge lines can then be connected.

In order to create the curved flow paths, the housing parts can each be welded together with a cover to form a closed conduit. The housing parts can be manufactured in an optimized manner from a small number of pieces. By mounting the covers as separate components at a later time, it is possible to insert cores into the conduits before the two subassemblies are welded together, and to remove said cores after the welding process. This prevents weld material from entering the passageways of the conduits.

A sensor device 1 shown in FIG. 1 includes a housing having four housing parts 2, 3, 4 and 5. Housing parts 2, 3, 4 and 5 are made of plastic and have a tubular port 6 and a tubular port 8 connected thereto on opposite sides thereof. Tubular port 6 constitutes an inlet and is formed with an enlarged collar 7 to which a supply line can be connected. Similarly, tubular port 8 has an enlarged collar 9 to which a discharge line can be connected. A fluid flowing into tubular port 6 is divided into two flow channels, as indicated by the arrows, and passed in a figure 8 pattern through the housing formed by housing parts 2, 3, 4 and 5 until it reaches tubular outlet port 8.

In the region of the intersection of the two flow channels, there are disposed a primary coil 10 and a secondary coil 11, it being possible to apply a voltage, for example, an AC voltage, to coil 10, so that, via the fluid passing through the housing, a conductor loop is formed and a voltage is induced in secondary coil 11, the induced voltage being proportional to the excitation voltage and to the conductivity of the conductor loop. Thus, under given boundary conditions, measurement of the induced voltage allows the conductivity of the traversing fluid to be measured with sufficient accuracy to determine the level of impurities in the fluid, which is advantageous especially for dishwashers and, in particular, when strict hygiene requirements must be met. Especially in the case of dishwashers used in hospital environments, this also makes it possible to document a cleaning process.

Housing parts 2, 3, 4, 5 are respectively provided with holding arms 13, 14, 15 and 16 for attachment of a printed circuit board. Thus, the sensor device can be constructed compactly and, in addition, may also include an evaluation and control unit, if necessary.

The production of the sensor device will now be described in more detail with reference to FIGS. 2 through 6.

Figure 2:
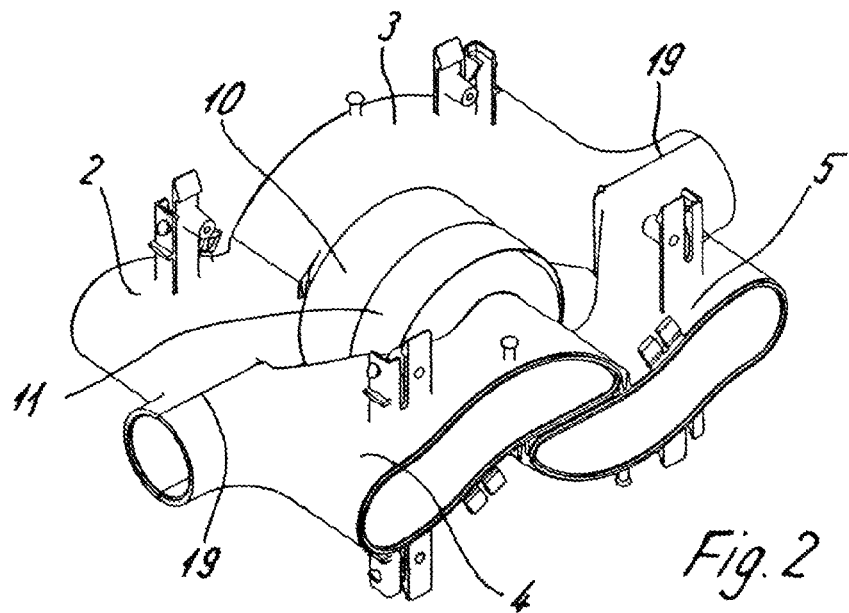
FIGS. 2-6 are perspective views showing different steps in the manufacture of the sensor device of the present invention.
Figure 3:
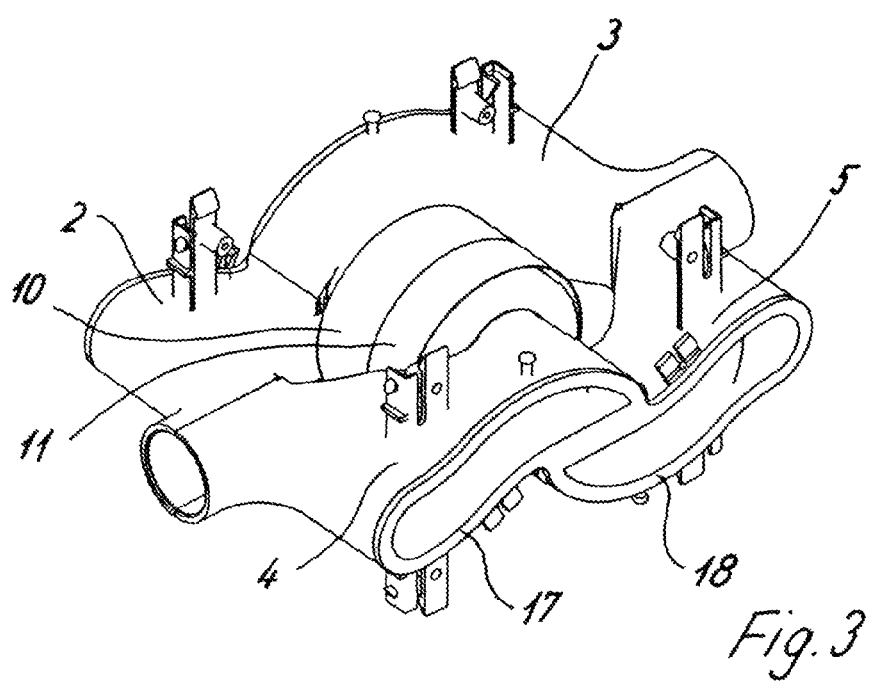

In a first step, housing parts 4 and 5 are joined together to form a first subassembly. Suitable clamping or snap-fit means may be provided for fixing purposes. Then, primary coil 10 and secondary coil 11 are slipped onto a central portion of the two housing parts 4 and 5. After that, the two housing parts 2 and 3, which may be constructed identically to housing parts 4 and 5, are also joined together by clamping or snap-fit means to form a subassembly, and are welded to housing parts 4 and 5 along a parting plane 19, as is shown in FIG. 2. The two subassemblies, as shown, are identical.

Housing parts 2, 3, 4 and 5 are initially open on the sides facing away from primary coil 10 and secondary coil 11, and are then closed by two covers 17 and 18. In the exemplary embodiment shown in FIG. 3, the covers are formed in one piece, respectively; a cover 17 closing housing part 4 and a cover 18 closing housing part 5. Housing parts 2 and 3 are similarly closed by a cover 17, 18, respectively.

Figure 4:
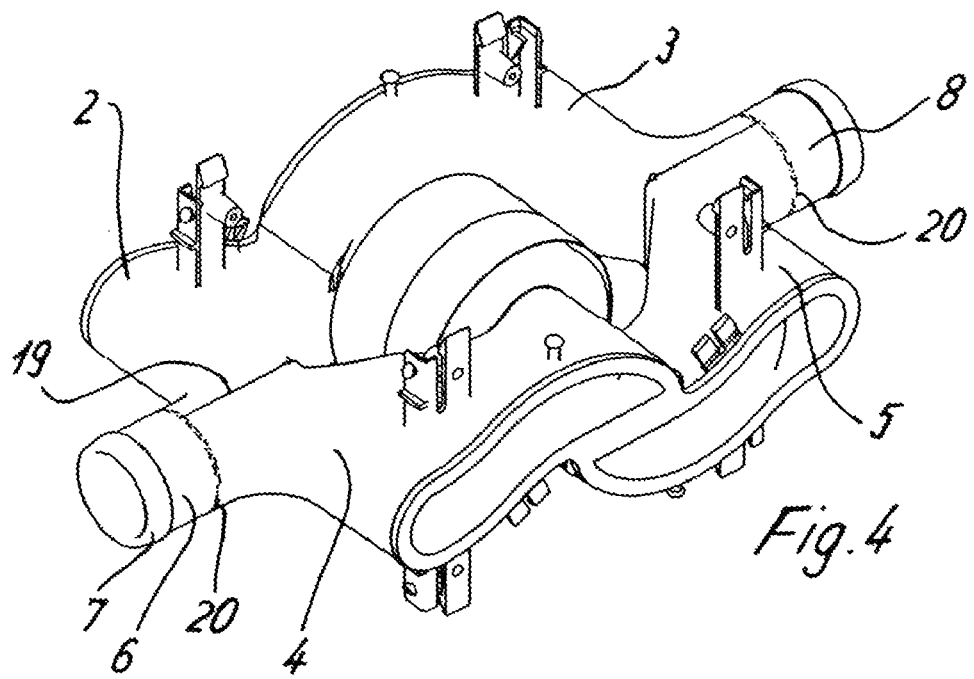

Referring to FIG. 4, in another step, a tubular port 6 is welded to housing parts 2 and 4 to form an inlet, a weld 20 being formed in the process. This ensures that the area of attachment of the lines is not located in the region of parting plane 19 between housing parts 2 and 4, where small burrs may be formed during the welding process.

On the opposite side, a tubular port 8 is similarly welded to housing parts 3 and 5 to form an outlet.

Figure 5:
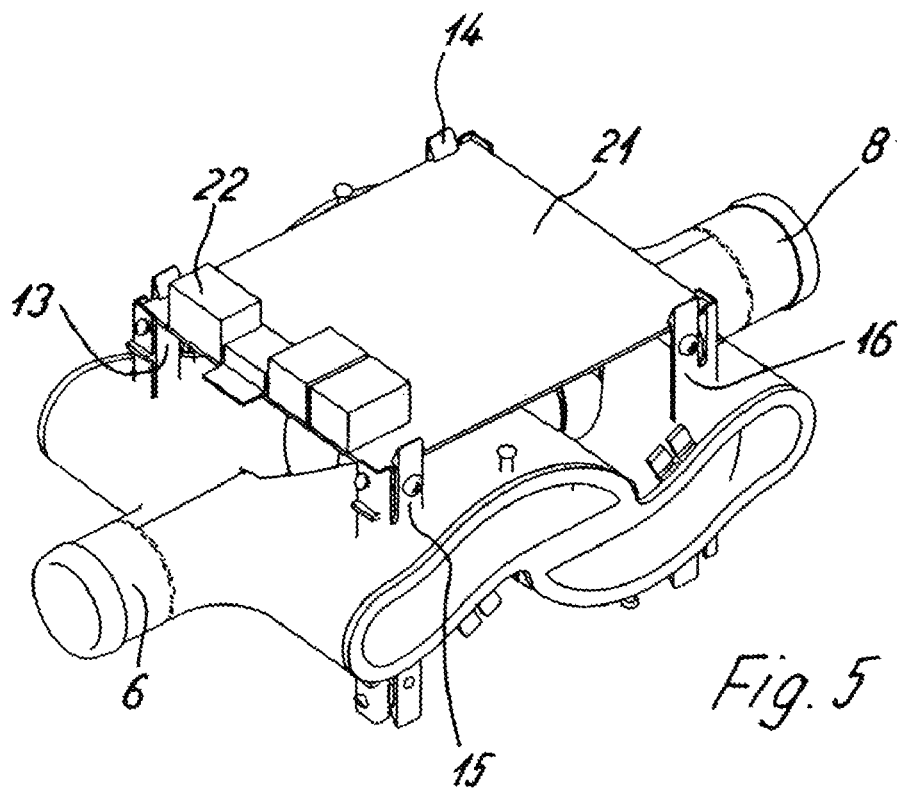

Referring to FIG. 5, in another step, a printed circuit board 21 is mounted to holding arms 13, 14, 15 and 16, provision being made for suitable snap-fit means. Printed circuit board 21 may have provided thereon suitable electronic components 22 for measuring and evaluating the conductivity of a traversing fluid. It is also possible to provide control elements on printed circuit board 21.

Figure 6:
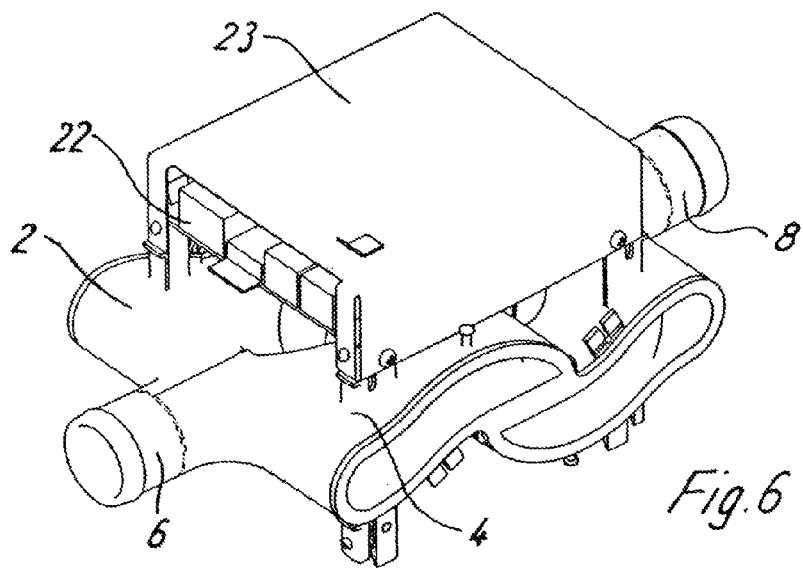

In FIG. 6, the sensor device is shown in a fully assembled condition. Printed circuit board 21 is covered by a housing 23 which is screwed to holding arms 13, 14, 15 and 16. The sensor device can be installed on an appliance, such as a dishwasher; a supply line and a discharge line are connectable to tubular ports 6 and 8, respectively.

Figure 7:
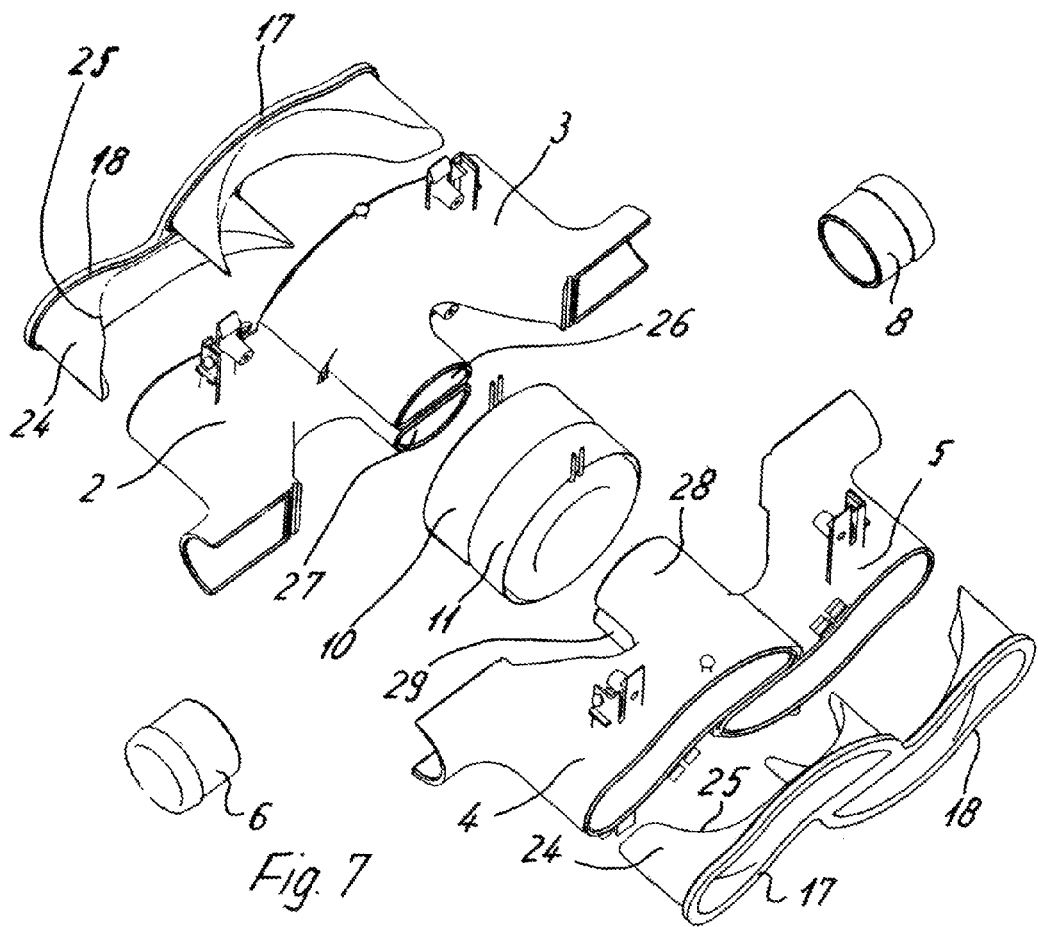
FIG. 7 is an exploded view of the sensor device of FIG. 1.

In FIG. 7, the sensor device is shown in an exploded view which shows, in particular, the outlines of covers 17 and 18. The covers have projections 24 formed on opposite sides thereof, the projections being able to be inserted into housing parts 2, 3, 4, 5 and having a reduced thickness toward the center of covers 17 and 18, so that a curved wall 25 is formed which provides a curved flow channel having low frictional losses.

Also shown is a central portion of housing parts 2, 3, 4 and 5, which is insertable into primary coil 10 and secondary coil 11. Housing part 2 includes a central portion 27 which is semicircular in cross-section and which is welded to a central portion 29 of housing part 5. Central portion 26 of housing part 3, which is also semicircular in cross-section, is similarly connected to central portion 28 of housing part 4. The welding together of the central portions 27 and 29, of central portions 26 and 28, and of the two subassemblies formed by housing parts 2, 3, 4 and 5 along parting plane 19 is accomplished using a hot plate welding method. Cores are inserted into the central portions to prevent weld material from entering the cross-sections of the conduits. After the two subassemblies are joined, the cores can be removed through the openings, which, in the next step, are closed by covers 17 and 18. Thus, in the region of primary coil 10 and secondary coil 11, the fluid is directed in opposite directions; contact of the fluid being prevented in this region in order to prevent flow resistances.

In the exemplary embodiment shown, four identically constructed housing parts 2, 3, 4 and 5 are provided which are assembled to form a housing of the sensor device. Of course, housing parts 2 and 3 and housing parts 4 and 5 can also be formed in one piece, respectively, so that only two housing parts are joined together. Moreover, covers 17 and 18 are respectively mounted on housing parts 2, 3, 4 and 5 to form a closed flow channel. Of course, it is also possible to provide a separate cover for each of the housing parts 2, 3, 4 and 5.

What is claimed is:

1. A sensor device comprising:
 a coil arrangement including a primary coil and a secondary coil; and
 a conduit traversable by a flow in a figure-8 pattern and disposed as a yoke about the coil arrangement such that the coil arrangement is disposed in a vicinity of an intersection of the figure-8 pattern, the conduit including at least two parts, a parting plane of the at least two parts configured so as to enable the coil arrangement to be slip-fit mounted on the conduit before a joining together of the two parts.

2. The sensor device as recited in claim 1, wherein the sensor device is a conductivity sensor for a dishwasher.

3. The sensor device as recited in claim 1, wherein at least one of the at least two parts is a subassembly.

4. The sensor device as recited in claim 1, wherein the parting plane is perpendicular to a plane defined by the figure-8 pattern.

5. The sensor device as recited in claim 1, wherein the conduit is formed by only two parts.

6. The sensor device as recited in claim 1, wherein the conduit includes at least two flow channels traversing the intersection of the figure-8 pattern, and
wherein the at least two flow channels are separate at the intersection of the figure-8 pattern.

7. The sensor device as recited in claim 1, further comprising an inlet disposed on a first loop of the figure-8 pattern and an outlet disposed on a second loop of the figure-8 pattern.

8. The sensor device as recited in claim 7, further comprising a respective tubular port welded to each of the inlet and outlet and operable to connect to a supply line or a discharge line, respectively.

9. The sensor device as recited in claim 1, wherein the at least two parts includes four identical housing parts and further comprising at least two covers joining the housing parts so as to form the conduit, the conduit being a closed conduit.

10. The sensor device as recited in claim 9, wherein each of the covers is formed as a separate part from the housing parts.

11. The sensor device as recited in claim 9, wherein each housing part includes a holding arm operable to attach a printed circuit board.

12. The sensor device as recited in claim 9, wherein the covers engage the housing parts so as to form a curved flow path.

13. A method of making a sensor device comprising:
receiving a first coil onto a first central conduit portion of a first subassembly;
receiving a second coil onto a second central conduit portion of a second subassembly;
welding the first subassembly to the second subassembly so as to form a section of a branched conduit traversable by flow in a figure-8 pattern.

14. The method as recited in claim 13, wherein the section of branched conduit includes housing parts of the first and second subassemblies.

15. The method as recited in claim 13, further comprising:
inserting cores into the subassemblies before the welding; and
removing the cores from the subassemblies after the welding.

16. The method as recited in claim 15, further comprising welding a respective tubular port to each of an inlet and an outlet of the branched conduit.

17. The method as recited in claim 13, wherein the subassemblies include housing parts and further comprising welding a cover to the housing parts so as to form a closed conduit.

18. A method of making a sensor comprising:
providing first and second subassemblies which together form a branched conduit having a figure-8 pattern such that a flow path of the branched conduit is split into two flow path sections that cross paths at a cross-section of the figure-8 pattern and rejoin toward an outlet of the sensor, the first assembly including a first central conduit portion corresponding to the cross-section of the figure-8 pattern and the second assembly including a second central conduit portion corresponding to the cross-section of the figure-8 pattern;
disposing a first coil about the first central conduit portion;
disposing a second coil about the second central conduit portion; and
welding the first central conduit portion to the second central conduit portion so as to form the branched conduit.

19. The method as recited in claim 18 wherein each subassembly includes a plurality of conduit sections and the method further comprising:
inserting a core into each conduit section prior to welding the first and second central conduit portions; and
removing the core from each conduit section after welding the first and second central conduit portions.

20. The method as recited in claim 18 wherein each subassembly includes a first housing part including a first conduit section that is part of the first flow path section and a second housing part including a second conduit section that is part of the second flow path section, the method further comprising;
welding a cover to each housing part so as to close the respective conduit section.

\* \* \* \* \*